United States Patent [19]

Muto et al.

[11] Patent Number: 4,681,877

[45] Date of Patent: Jul. 21, 1987

[54] PIVALOYLOXYMETHYL
7-β-[2-(2-AMINO-4-THIAZOLYL)-2-
METHOXYIMINOACETAMIDO]-3-(2-
AMINO-1,3-THIADIAZOLYL-5-THIOME-
THYL)-3-CEPHEME-4-CARBOXYLATE AND
PHARMACEUTICAL COMPOSITION
CONTAINING THE SAME

[75] Inventors: Shigeaki Muto; Takao Ando;
Takayoshi Fujii; Akihiko Kanno, all
of Tokyo; Yoko Onishi, Mitaka;
Isamu Motokawa, Hino; Takao
Furusho, Machida; Chikao
Yoshikumi, Kunitachi, all of Japan

[73] Assignee: Kureha Kagaku Kogyo Kabushiki
Kaisha, Tokyo, Japan

[21] Appl. No.: 562,003

[22] Filed: Dec. 16, 1983

[30] Foreign Application Priority Data

Dec. 24, 1982 [JP] Japan .................. 57-233697
Mar. 1, 1983 [JP] Japan .................. 58-33579

[51] Int. Cl.⁴ .................. A61K 31/545; C07D 501/36
[52] U.S. Cl. .................. 514/206; 540/227
[58] Field of Search .................. 544/27; 514/206

[56] References Cited

U.S. PATENT DOCUMENTS 4,189,479 2/1980 Kakeya et al. .................. 544/27
4,278,793 7/1981 Durckheimer .................. 544/25

FOREIGN PATENT DOCUMENTS 0002774 11/1979 European Pat. Off. .
2348218 10/1977 France .

OTHER PUBLICATIONS

Godtfredson et al., "Pivaloyloxymethy in Ceph-3-- Em-4-Carboxylate," . . . *Chem. Abst.*, 72:13276i(v) (1970).
Tinti et al., "Synthesis of 7-(Acylamido)deacetoxycephalosporanic Acids and . . . Esters . . . ", *Chem. Abst.*, 92:94332j (1979).

*Primary Examiner*—Donald G. Daus
*Assistant Examiner*—G. Hendricks
*Attorney, Agent, or Firm*—Oblon, Fisher, Spivak, McClelland & Maier

[57] ABSTRACT

Disclosed herein are 7-beta-[2-(2-amino-4-thiazolyl)-2-methoxyiminoacetamido]-3-(2-amino-1,3,4-thiadiazolyl-5-thiomethyl)-3-cepheme-4-carboxylic acid, salts thereof and pivaloyloxymethyl ester thereof, and a pharmaceutical composition containing the same as an active ingredient.

4 Claims, 3 Drawing Figures

PIVALOYLOXYMETHYL 7-β-[2-(2-AMINO-4-THIAZOLYL)-2-METHOXYIMINOACETAMIDO]-3-(2-AMINO-1,3-THIADIAZOLYL-5-THIOMETHYL)-3-CEPHEME-4-CARBOXYLATE AND PHARMACEUTICAL COMPOSITION CONTAINING THE SAME

BACKGROUND OF THE INVENTION

The present invention relates to 7-beta- [2-(2-amino-4-thiazolyl)-2-methoxyiminoacetamido]-3-(2-amino-1,3,4-thiadiazolyl-5-thiomethyl) -3-cepheme-4-carboxylic acid represented by the formula(I):

and the derivatives thereof and a pharmaceutical composition containing the same as an active ingredient. More in detail, the present invention relates to 7-beta-[2-(2-amino-4-thiazolyl)-2-methoxyiminoacetamido]-3-(2-amino-1,3,4-thiadiazolyl-5-thiomethyl)-3-cepheme-4-carboxylic acid, salts thereof and pivaloyloxymethyl ester thereof, and a pharmaceutical composition containing 7-beta- [2-(2-amino-4-thiazolyl)-2-methoxyiminoacetamido]-3-(2-amino-1,3,4-thiadiazolyl-5-thiomethyl)-3-cepheme-4-carboxylic acid, a pharmaceutically acceptable salt thereof or pivaloyloxymethyl ester thereof as an active ingredient.

Still more in detail, the pharmaceutical composition according to the present invention contains 7-beta- [2-(2-amino-4-thiazolyl) -2-methoxyiminoacetamido]-3-(2-amino-1,3,4-thiadiazolyl -5-thiomethyl)-3-cepheme-4-carboxylic acid which has a remarkably improved stability in blood of a living body while still retaining the antimicrobial activity of the so-called third generation antibiotics derived from cephalosporin by virtue of modifying 3-position of the so-called third antibiotics derived from cephalosporin by a 2-amino-1,3,4-thiazolyl-5-thiomethyl group, a pharmaceutically acceptable salt or pivaloyloxymethyl ester thereof as an active ingredient.

Cephalosporin antibiotics are broadly utilized at present because of their excellent anti-bacterial activity, however, although they have various merits of showing activity against both gram-positive and gram-negative bacteria in a broad range and of being stable to beta-lactamase, they have a serious demerit of being low in stability in blood of the host resulting in a short active life thereof in the host when administered thereto. As a result of the present inventors' studies for finding an antibiotic showing a cephalosporin-like activity without losing its activity even in the blood of the host, it has been found that 7-beta- [2-(2-amino-4-thiazolyl)-2-methoxyiminoacetamido]-3-(2-amino-1,3,4-thiadiazolyl-5-thiomethyl)-3-cepheme-4-carboxylic acid represented by the formula(I) and some derivatives thereof are effective in the above-mentioned sense, and the present inventors have attained the present invention.

SUMMARY OF THE INVENTION

In a first aspect of the present invention, there is provided 7-beta-[2-(2-amino-4-thiazolyl)-2-methoxyiminoacetamido]-3-(2-amino-1,3,4,-thiadiazolyl-5-thiomethyl)-3-cepheme-4-carboxylic acid represented by the formula(I):

salts thereof and pivaloyloxymethyl ester thereof.

In a second aspect of the present invention, there is provided a process for producing 7-beta-[2-(2-amino-4-thiazolyl)-2-methoxyiminoacetamido]-3-(2-amino-1,3,4,-thiadiazolyl-5-thiomethyl)-3-cepheme-4-carboxylic acid represented by the formula (I):

comprising the steps of reacting 2-methoxyimino-2-(2-formylamino-1,3-thiazolyl)acetic acid represented by the formula(II):

with a compound represented by the formula(III):

in an organic solvent at a temperature of −30° to 50° C. for 0.5 to 48 hours to obtain a diformyl compound and subjecting the thus obtained diformyl compound to deformylation.

In a third aspect of the present invention, there is provided a process for producing pivaloyloxymethyl 7-beta-[2-(2-amino-4-thiadiazolyl -2-methox-yiminoacetamido]-3-(2-amino-1,3,4-thiadiazolyl-5-thiomethyl) -3-cepheme-4-carboyxylate represented by the formula(V):

comprising the steps of reacting 2-methoxyimino-2-(2-formylamino-1,3-thiazolyl)acetic acid represented by the formula(II):

with a compound represented by the formula(III):

in an orgainc solvent at a temperature of −30° to 50° C. for 0.5 to 48 hours to obtain a diformyl compound, subjecting the thus obtained diformyl compound to deformylation to obtain 7-beta-[2-(2-amino-4-thiazolyl) -2-methoxyiminoacetamido]-3-(2-amino-1,3,4-thiadiazolyl-5-thiomthyl)-3-cepheme-4-carboxylic acid represented by the formula(I):

and reacting the thus obtained carboyxlic acid compound or the salt thereof obtained by neutralization thereof with a compound represented by the formula(IV):

$$XCH_2OCOC(CH_3)_3 \qquad (IV)$$

wherein X represents a halogen atom, in an organic solvent at a temperature of −30° to 50° C. for 0.5 to 48 hours.

In a fourth aspect of the persent invention, there is provided an antibacterial agent containing 7-beta-[2-(2-amino-4-thiazolyl) -2-methoxyiminoacetamido]-3-(2-amino-1,3,4-thiadiazolyl5-thiomethyl)-3-cepheme -4-carboxylic acid represented by the formula(I), a pharmaceutically acceptable salt threof or pivaloyloxymethyl ester thereof as an active ingredient:

In a fifth aspect of the present invention, there is provided a pharmaceutical composition in dosage unit form which comprises an effective dosage of 7-beta-[2-(2-amino-4-thiazolyl)-2-methoxyiminoacetamido ]-3-(2-amino-1,3,4-thiadiazolyl-5-thiomethyl)-3-cepheme-4-carboxylic acid represented by the formula (I), a pharmaceutically acceptable salt thereof or pivaloyloxymethyl ester thereof as a main component and a pharmaceutucally acceptable carrier or diluent.

In a sixth aspect of the present of the present invention, there is provided a method for the treatment of infectious diseases caused by bacteria which comprises administering an effective amount of a compound of 7-beta- [2-(2-amino-4-thiazolyl)-2-methoxyiminoacetamido]-3-(2-amino-1,3,4-thiadiazolyl-5-thiomethyl)-3-cephmem -4-carboxylic acid represented by the formula (I):

(I)

a pharmaceutically acceptable salt thereof or pivaloyloxymethyl ester thereof.

BRIEF EXPLANATION OF DRAWINGS

Of the attached drawings.

DETAILED EXPLANATION OF THE INVENTION

The compound according to the present invention is 7-beta- [2-(2-amino-4-thiazolyl)-2-methoxyiminoacetamido]-3-(2-amino -1,3,4-thiadiazolyl-5-thiomethyl)-3-cepheme--4-carboxylic acid represented by the formula(I):

(I)

salts thereof or pivloyloxymethyl 7-beta-[2-(2-amino-4-thiazolyl) -2-methoxyiminoacetamido]-3-(2-amino-1,3,4-thiadiazolyl-5-thiomethyl)-3-cepheme -4-carboxylate represented by the formula(V):

(V)

Although the compound represented by the formula (I) is an antibiotic substance derived from cephalosporin oxime, it is an antibiotic of a new type having its 3-position of the dihydrothiazine ring modified by a 2-amino-thiadiazolyl-5-thiomethyl group, thereby having improved the stability in blood of living body and showing an extremely low acute mammalian toxicity, and accordingly, the compound is an extremely safe substance in that sense.

The compound represented by the formula(V) is another antibiotic substance obtained by further modifying the carboxylic group of the compound represented by the formula(I).

Namely, the compound represented by the formula(V) is an antibiotic of a new type in that when it is administered orally or intestinally to the host, it is absorbed into the host body without giving any effects on the useful bacterial colonies habitually present in the intestines of the host and it exhibits its antibacterial activity at the first time after entering into the blood of the host. It is also a quite safe material showing a very low mammalian acute toxicity.

The compound represented by the formula(I) is obtained by the following process.

Into a solution prepared by dissolving 2-methoxyimino-2-(2-formylamine 1,3-thiazolyl)acetic acid represented by the formula(II) in an organic solvent, for instance, dimethylformamide, acetone, ethyl acetate, benzene, dichloromethane, pyridine, tetrahydrofuran or dioxane:

(II)

a solution prepared by dissolving a compound represented by the formula(III):

in an organic solvent, for instance, dimethylformamide, acetone, ethyl acetate, benzene, dichloromethane, pyridine, tetrahydrofuran or dioxane is added to carry out a reaction between the two compounds at −30° to 50° C. for 0.5 to 48 hours, and after the reaction is over, the product, a diformyl compound, is collected by means of washing with a solvent or extracting with a solvent and purified by recrystallization.

It is preferable that carbodiimide, ethyl chlorocarbonate, ethyl oxalyl chloride or phosphorus oxychloride dissolved in dimethylformamide is preliminarily added as an activator to the solution containing the compound represented by the formula(II). It is preferable that in the case of adding a solution containing the compound represented by the formula (III) into the solution containing the compound represented by the formula(II), a silylization agent such as N-trimethylsilylacetamide and N,O-bis(trimethylsilyl)acetamide is added to the mixture of the respective two solutions.

Then, the thus obtained diformyl compound is treated by a known method of de-formylation to be converted to the compound represented by the formula(I).

The alkali metal salt, for instance, sodium salt and potassium salt, the alkaline earth metal salt, for instance, calcium salt and magnesium salt, ammonium salt, trimethylamine salt, or dicyclohexylamine salt of the compound represented by the formula(I):

is obtained by neutralizing the compound represented by the formula(I) according to the conventional method.

The compound represented by the formula(V):

is obtained by adding a compound represented by the formula(IV) XCH$_2$OCOC(CH$_3$)$_3$ wherein X is a halogen atom such as an atom of chlorine, bromine or fluorine into a solution prepared by dissolving the compound represented by the formula(I):

namely, 7-beta-[2-(2-amino-4-thiazolyl)-2-methoxyiminoacetamido]-3-(2-amino-1,3,4-thiadiazolyl-5-thiomethyl)-3-cepheme-4-carboxylic acid, or a salt thereof in an organic solvent, for instance, dimethylformamide, dimethylsulfoxide, dimethylacetamide or pyridine, and bringing them into reaction at a temperature of −30° to 50° C. for 0.5 to 48 hours, and collecting the object compound by means of washing with a solvent, extracting with a solvent, column chromatography and recrystallization. It is preferable to add an amine such as triethylamine and dicyclohexylamine or a basic substance such as sodium hydroxide and sodium hydrogencarbonate preliminarily into the solution containing the compound represented by the formula(I).

The pharmacological properties of the compound represented by the formula(I) and the compound represented by the formula(V) were investigated as follows:

(a) Acute mammalian toxicity

Acute mammalian toxicity of the compound represented by the formula(I) and the compound represented by the formula(V) was investigated by orally or intraperitoneally administering a series of aqueous physiological saline solution containing each of the above-mentioned compounds to groups of ICR-JCL mice, and observing the toxic symptoms appearing on the mice including the mortality for 7 days. Then, from the cumulative mortality, LD$_{50}$ values were calculated by Litchfield-Wilcoxon's graphical method.

As the result, both $LD_{50}$(oral) and $LD_{50}$(intraperitoneous) of the compound represented by the formula(I) or the salts thereof and the compound represented by the formula(V) were higher than 10 g/kg body weight. No noticeable information was obtained on the autopsy carried out after 7 days of the administration on the dead mice and the live mice.

(b) Effect on the intestinal bacteria

After collecting the feces of a group of mice, the compound represented by the formula(V) was orally administered thereto for 2 days at a daily dose of 100 mg/kg body weight and the feces were collected one day after the 2 days. Each portion of the two kinds of the feces was cultured at 25° C. or 37° C. in a variety of culture medium for one to five days to see the state of *Escherichia coli, Pseudomonas aeruginosa*, a *Streptococcus* species, lactic acid bacteria, *Lactobacillus bifidus* and bacteroid bacteria in the culture medium.

As a result, the number of colonies of each bacterial species showed no change between before and after the administration of the compound represented by the formula(V), the result telling that the compound gives no effect on the intestinal bacterial colonies.

(c) Anti-bacterial activity

The minimum inhibiting concentration(MIC) of the compound represented by the formula(I) and the compound represented by the formula(V) was measured according to the standard method of Japan Society of Chemotherapy against each of the following bacterial species:

*Escherichia coli* IFO 12734
*Staphylococcus aureus* IAM 1011
*Escherichia coli* W 3636
*Proteus vulgaris* IAM 1025
*Pseudomonas aeruginosa* IAM 1514 and
*Serratia marcescens* IAM 1223

As will be shown in Example 4, the compound represented by the formula(I) exhibited a strong and broad anti-bacterial activity as it is against the test bacterial species. While MIC of the compound represented by the formula(V) was not so small to verify the anti-bacterial activity thereof.

(d) Anti-bacterial activity of the compound represented by the formula(V), exhibited after being absorbed in living body After preparing a preliminary culture liquid containing $10^8$ cells of *Staphylococcus aureus* IAM 1011 per ml and adding ing 10 the cultured liquid to 50 times by weight of Mueller-Hinton agar culture medium, flat culture plates were prepared. On the thus prepared flat culture plate, three penicillin cups were placed, and each of the compounds to be tested was placed in each cup with or without an addition of 0.1 ml of a cultured material of rat liver homogenate(referred to as S-9 mix).

After incubating the thus prepared flat culture plates for 18 hours at 37° C., the diameter of each of the growth-inhibiting circle around the penicillin cups was measured.

The results were as follows.

When the diameter of growth-inhibition circle formed by the compound represented by the formula(I) was represented by 100, the diameter of growth-inhibition circle formed by the sodium salt thereof was nearly 100 and the diameter of growth-inhibition circle formed by the compound represented by the formula(V) was 0 to 1. On the other hand, the diameter of growth-inhibition circle formed by the compound represented by the formula(V) added with S-9 mix was 67 to 100. The results show that although the compound represented by the formula(V) is very low in anti-bacterial activity, it is activated by S-9 mix, the rat liver homogenate, and it will be also activated in the body of the mouse.

(e) Effects on infectious disease

In order to confirm the activation of the compound represented by the formula(V) in living body, the following experimental treatment was carried out.

After inoculating a group consisting of 20 mice with *Escherichia coli* IFO intraperitoneously to be infected, the compound represented by the formula(V) was orally administered to the mice just after and after 4 hours of inoculation at a dose rate of 100 mg/kg body weight, and after 7 days of the administration, the effectiveness of the compound was judged by observing the death rate of each group of mice by the infection.

The rate of survival of the group administered with the compound represented by the formula(V) was over 60%, the result showing the effectiveness of the compound represented by the formula(V) as an anti-infectious disease medicine to be orally administered.

In the same manner, after inoculating another group consisting of 20 mice with *Escherichia coli* IFO intraperitoneously to be infected, the compound represented by the formula(I) was orally administered thereto just after and after 4 hours of inoculation at the dose rate of 100 mg/kg body weight, and after 7 days of the administration, the effectiveness of the compound was judged by observing the rate of survival of the mice.

The rate of survival of the group administered with the compound represented by the formula(I) was over 55%, the result showing the effectiveness of the compound represented by the formula(I) as an anti-infectious disease medicine to be orally administered.

Namely, the compound represented by the formula(V) is safe and has no effect on the intestinal bacterial colonies of the host to which the compound has been administered, and in addition, it becomes to be active after being absorbed into the living body of the host. In this sense, the compound represented by the formula(V) can be said to be a new type of cephalosporin-like antibiotic substance, and because of its activation in the living body to exhibit the cephalosporin-like anti-bacterial activity, the compound represented by the formula(V) can be used as an antibiotic in quite the same field as that in which cephalosporins are used as antibiotics.

The compound represented by the formula(I), the pharmaceutically acceptable salt thereof and the compound represented by the formula(V) can be used as an active ingredient in a pharmaceutical composition in dosage unit form by oral administration, injectional administration or rectal administration.

Oral administration may be effected by the types of the pharmaceutical composition of tablets, capsules, powders, granules, pills and ampules, which contain filler(s), extenders, binders, wetting agents, disintegrators, dissolution-retarders, reabsorption-accelerators, adsorbing carriers, and wetting agents.

As the definite adjuvant, starch, mannitol, silicic acid, derivatives of cellulose, gelatin, alginates, glycerol, agar, calcium carbonate, sodium hydrogencarbonate, paraffin, quarternary ammonium salts, glycerol monostearate, kaolin, bentonite, talc, potassium stearate, magnesium stearate and polyethylene glycol may be mentioned.

In addition, the pharmaceutical composition may take the form of a pharmaceutically acceptable emulsion, solution or suspension.

The pharmaceutical composition for rectal administration, that is suppository, may contain polyethylene glycol and fatty acid or an ester thereof.

Syrup and elixir comprising the compound represented by the formula(I), a pharmaceutically acceptable salt or the compound represented by the formula(V) may contain an inert diluent such as water and paraffin, and may be used as a liquid composition suitable for oral administration. Adjuvants such as a wetting agent, sweetener and seasoning may be contained therein.

The composition used for injective administration should be aseptic and may be an aqueous solution or non-aqueous solution, suspension or emulsion, and in addition, may contain propylene glycol, polyethylene glycol and olive oil.

The pharmaceutical composition may contain the compound represented by the formula(I), a pharmaceutically acceptable salt thereof or the compound represented by the formula(V) in an amount of 0.01 to 99.5% by weight, usually 0.1 to 90% by weight thereof.

The compound represented by the formula(I), a pharmaceutically acceptable salt or the compound represented by the formula(V) is used for the same purpose as that of the conventional antibiotics derived from cephalosporins and is effective in the treatment of infectious diseases caused by bacteria. The dose rate of the pharmaceutical composition depends on the degree of infection and the state of the patient, however, generally, 0.1 to 10 g (as the active ingredient) is daily administered after dividing into portions The present invention will be more precisely explained while referring to Examples as follows.

However, the present invention is not restricted to Examples under mentioned. From the foregoing description, one skilled in the art can easily ascertain the essential characteristics of the present invention, and without departing from the spirit and scope thereof, can make various changes and modifications of the invention to adapt it to various usages and conditions.

omethyl-3-cepheme-3-carboxylic acid and 8 g of trimethylsilyl acetamide was mixed at a temperature of $-10°$ C., and the mixture was stirred for one hour at a temperature of 0° C. to carry out a reaction. After the reaction was over, 20 ml of ethyl acetate were added to the reaction mixture to extract the reaction product. After washing the layer of ethyl acetate two times with an aqueous saturated solution of sodium chloride, the layer was dried on anhydrous sodium sulfate and after distilling the solvent, the residue was recrystallized from a mixed solvent of ethyl acetate and ethanol to obtain 2.8 g of the diformyl compound in a yield of 47%.

In a mixed solvent of 20 ml of methanol and 15 ml of tetrahydrofuran, the thus obtained diformyl compound was dissolved, and after adding 2 ml of conc. hydrochloric acid into the solution, the mixture was stirred for 2 hours at room tempreature. After the reaction was over, the organic solvent was distilled off from the reaction mixture, and the residue was adjusted to pH of 3.0 with the addition of an aqueous saturated solution of sodium hydrogen-carbonate under cooling by iced water. After stirring the mixture for 30 min while cooling, the thus precipitated crystals were collected by filtration and by drying the crystals, 1.1 g of pale yellow crystals melting at 151° to 158° C. with decomposition were obtained in a yield of 58%.

Figure 1:
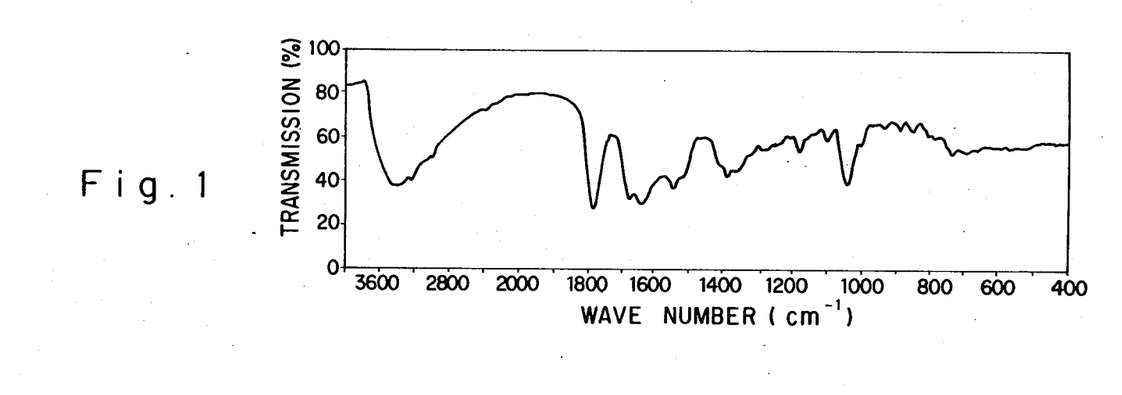
FIGS. 1 to 3 show infrared absorption spectrum of the compound according to the present invention obtained in Examples 1 to 3, respectively.

The thus obtained product, 7-beta- [2-(2-amino-4-thiazolyl)-2-methoyiminoacetamido]-3-(2-amino-1,3,4-thiadiazolyl -5-thiomethyl)-3-cepheme-4-carboxylic acid which is represented by the following formula(I) showed an infrared absorption spectrum with the following absorption maxima as a KBr-tablet(refer to FIG. 1): 3360, 3210, 1776, 1670, 1625, 1538 and 1040 cm$^{-1}$ and an ultraviolet absorption spectrum in ethanol with the following absorption maxima: 235 and 270 nm The elementary analytical data of the product were as follows:

|  | C (%) | H (%) | N (%) |
|---|---|---|---|
| Found | 36.40 | 3.11 | 21.10 |
| Calculated as $C_{16}H_{16}N_8O_5S_4$ | 36.36 | 3.03 | 21.21 |

(I)

EXAMPLE 1

Production of 7-beta-[2-(2-amino-4-thiazolyl)-2-methoxyiminoacetamido]-3-(2-amino-1,3,4-thiadiazolyl-5-thiomethyl)-3-cepheme-4-carboxylic acid Into Vilsmeier's reagent prepared by adding 0.86 ml of dimethylformamide and 1 ml of phosphorus oxychloride into 10 ml of ethyl acetate, 2.3 g of 2-(2-formylamino-4-thiazolyl)-2-methoxyiminoacetic acid were added little by little at a temperature of $-5°$ C. to be activated. Into the thus activated mixture, a solution of 3.7 g of 3-(2-formylamino-1,3,4-thiadiazolyl-5-thi-

EXAMPLE 2

Into 4 ml of aqueous 0.5 N solution of sodium hydroxide, 1.05 g of 7-beta- [2-(2-amino-4-thiazolyl)-2-methoxyiminoacetamido]-3-(2-amino-1,3,4-thiadiazolyl-5-thiomethyl)-3-cepheme-4-carboxylic acid obtained by Example 1 were dissolved, and after adjusting the pH of the solution to 7 by adding aqueous 0.1 N solution of sodium hydroxide, the solvent was distilled off from the solution. After dissolving the residue into 20 ml of methanol and filtering the solution, the filtrate was dropped into 200 ml of acetone while stirring the mixture. After collecting the thus formed crystals by filtration and washing the crystals well with acetone, the crystals were dried to obtain 0.98 g of white crystals of the sodium salt of the compound represented by the formula(I), melting at 201 to 208° C. with decomposition, in a yield of 90 %.

Figure 2:
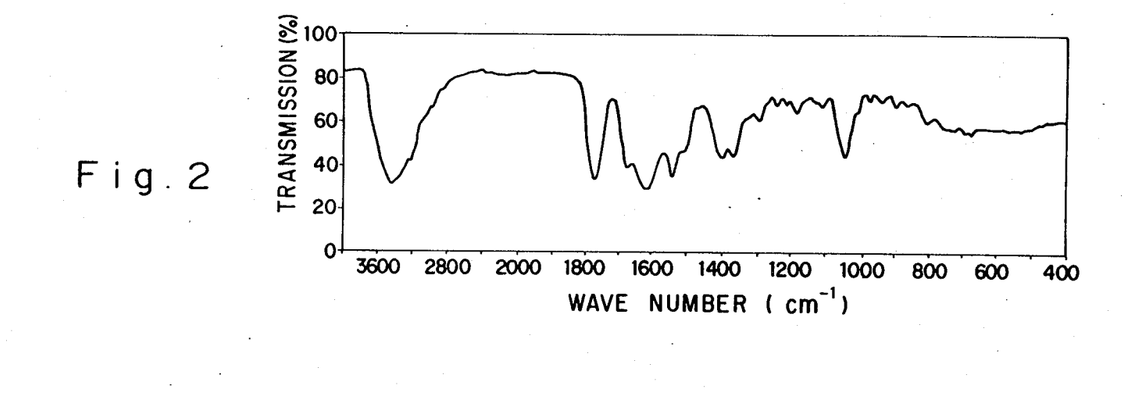

The thus obtained sodium salt showed an infrared absorption spectrum (refer to FIG. 2) with the following absorption maxima as a KBr tablet: 3450, 1775, 1677, 1612, 1541 and 1040 cm$^{-1}$, and an ultraviolet absorption spectrum with the following absorption maxima in water: 236 and 271 nm The elementary analytical data on the sodium salt were as follows:

|  | C (%) | H (%) | N (%) |
|---|---|---|---|
| Found | 35.24 | 2.77 | 20.44 |
| Calculated as $C_{16}H_{15}N_8O_5S_8Na$ | 35.16 | 2.75 | 20.51 |

EXAMPLE 3

Production of pivaloyloxymethyl 7-beta-[2-(2-amino-4-thiazolyl) -2-methoxyiminoacetamido]-3-(2-amino-1,3,4,- thiadiazolyl -5-thiomethyl)-3-cepheme-4-carboxylate Into 105 ml of N,N-dimethylformamide, 8.1 g of the product obtained in Example 1, 7-beta-[2-(2-amino-4-thiazolyl)-2-methoxyiminoacetamindo]-3-(2-amino-1,3,4-thiadiazolyl-5-thiomethyl) -3-cepheme-4-carboxylic acid, and 2.7 ml of dicyclohexylamine were dissolved, and after adding 3.9 g of bromomethyl pivalate into the solution, the mixture was stirred for 4 hours at room temperature. After removing the undissolved matters by filtration, the filtrate was subjected two times to decantation with each 750 ml of a 2:1 mixed solvent of n-hexane and ether, and 100 ml of water and 200 ml of ethyl acetate were added to the residue. After washing the organic layer two times with aqueous 5% solution of sodium hydrogencarbonate and two times with saturated aqueous solution of sodium chloride, the organic layer was dried on anhydrous sodium sulfate. After distilling the solvent off from the organic layer, the residue was purified by column chromatography(silica gel, with a mixed solvent of ethyl acetate and chloroform as an eluent) to obtain 3.2 g (yield: 32.5%) of crystals melting at 131 to 133° C. as the object product.

Figure 3:
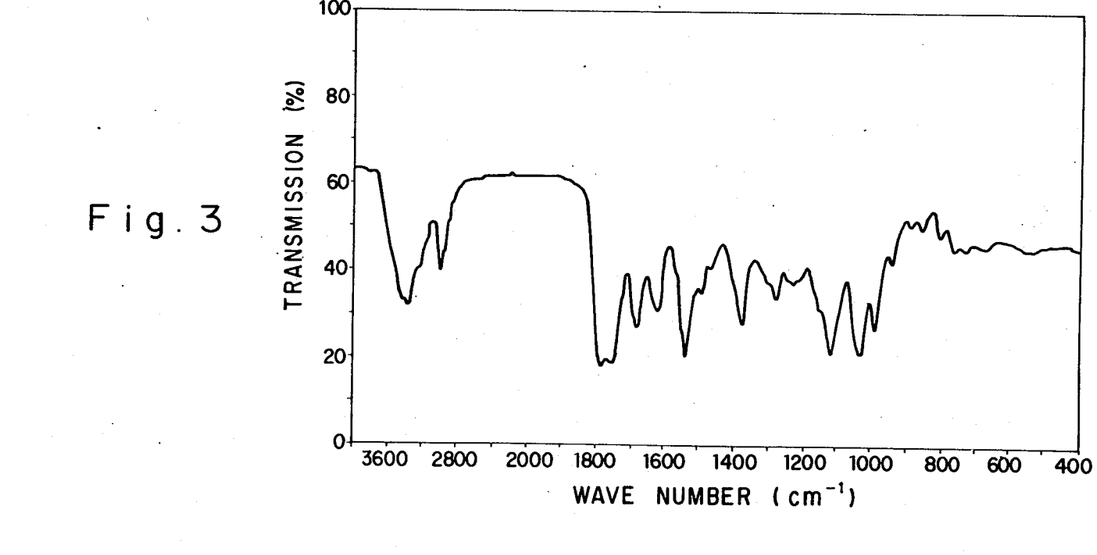

The object product, namely, pivaloyloxymethyl ester of the compound represented by the formula(I), which is represented by the following formula(V) showed an infrared absorption spectrum (refer to FIG. 3) with the following absorption maxima as a KBr tablet: 3380, 3000, 1785, 1765, 1538, 1117 and 1034 cm$^{-1}$ and an ultraviolet absorption spectrum with the following absorption maxima in ethanol: 234 and 262 nm The elementary analytical data of the product were as follows:

|  | C (%) | H (%) | N (%) |
|---|---|---|---|
| Found | 41.20 | 4.04 | 17.51 |
| Calculated as $C_{22}H_{26}O_7N_8S_4$ | 41.12 | 4.05 | 17.45 |

(V)

EXAMPLE 4

Determination of anti-bacterial activity of the respective products in Examples 1, 2 and 3

Anti-bacterial activity of the compounds respectively produced in Examples 1, 2 and 3 was determined according to the standard method of Japanese Society of Chemotherapy as follows.

Each of the following bacterial strains was inoculated in Mueller-Hinton's culture medium and cultured for 18 to 48 hours at 37° C. to obtain a standard bacterial liquid containing 10$^6$ cells/ml.

Bacterial strains:
*Escherichia coli IFO* 12734,
*Staphylococcus aureus IAM* 1011,
*Escherichia coli W* 3636,
*Proteus vulgaris IAM* 1025,
*Pseudomonas aeruginosa IAM* 1514 and
*Serratia marcescens IAM* 1223.

Separately, agar plates were prepared by adding each of the solutions of each of the compounds respectively produced in Examples, 1, 2 and 3 at predetermined concentrations in amount of one ninth by weight to Mueller-Hinton's culture medium.

After inoculating each of the above-mentioned bacterial liquid onto each of the agar plates by smearing as a line of about 2 cm in length, the inoculated agar plates were cultured for 18 to 24 hours at 37° C., and by examining the concentration of each compound which has completely inhibited the growth of each bacterial strain, the minimum concentration of inhibiting the growth of the bacterial strain was determined. The results are shown in Table 1.

TABLE 1

| | Minimum growth-inhibition concentration (MIC) on | | | | | |
|---|---|---|---|---|---|---|
| Compound produced in | E. coli IFO 12734 | Staphylococcus aureus IAM 1011 | E. coli W 3636 | Proteus vulgaris IAM 1025 | Pseudomonas aeruginosa IAM 1514 | Serratia marcescens IAM 1223 |
| Example 1 | <0.05 | 0.78 | 0.2 | <0.05 | 12.5 | 0.2 |
| Example 2 | <0.05 | 0.78 | 0.1 | <0.05 | 12.5 | 0.2 |

TABLE 1-continued

| | Minimum growth-inhibition concentration (MIC) on | | | | | |
|---|---|---|---|---|---|---|
| Compound produced in | E. coli IFO 12734 | Staphylococcus aureus IAM 1011 | E. coli W 3636 | Proteus vulgaris IAM 1025 | Pseudomonas aeruginosa IAM 1514 | Serratia marcescens IAM 1223 |
| Example 3 | 12.5 | ≧100 | 50 | 12.5 | ≧100 | ≧100 |
| CEFOTAX ® *1 | <0.05 | 1.56 | 0.1 | <0.05 | 50 | 0.2 |

Note:
*1A derivative of cephalosporin, manufactured by Hoechst A. G.

EXAMPLE 5

Effects of pivaloyloxymethyl 7-beta-[2-(2-amino-4-thiazolyl) -2-methoxyiminoacetamido]-3-(2-amino-1,3,4thiadiazolyl -5-thiomethyl)-3-cepheme-4-carboxylate on the intestinal bacterial colonies The above-mentioned pivaloyloxymethyl ester represented by the formula(V) was orally administered for two continued days at a daily dosage of 100 mg/kg body weight to each of five female ICR mice of a group after 6 weeks of birth.

Each of the two fecal specimens respectively collected before and after one day of the administration was diluted with 100 times by weight of an anaerobic diluent(a phosphoric buffer solution) and was ground in a mortar, and 0.1 ml of the ground material was smeared on each of the following culture media for the following bacteria and the thus inoculated culture media were incubated under the following conditions. Thereafter, the number of the following bacteria was determined on each culture medium.

| Culture media and conditions of the culture | | |
|---|---|---|
| Bacterial species | Culture medium | Conditions in culture |
| Escherichia coli | DHL agar | 37° C., for 1 day, aerobic |
| Pseudomonas aeruginosa | NAC agar | 37° C., for 1 day, aerobic |
| a species of Streptococcus | TATAC agar | 37° C., for 1 day, aerobic |
| a species of Lactobacillus | LBS agar | 37° C., for 5 days, anaerobic |
| Lactobacillus bifidus | BS agar | 37° C., for 1 day, anaerobic |
| a species of Bacteroides | NBGT agar | 37° C., for 1 day, anaerobic |

The results are shown in Table 2. As will be seen in Table 2, the number of cells of each of the bacterial strains did not show any noticeable change between before and after the administration of the pivaloyloxymethyl 7-beta-[2-(2-amino-4-thiazolyl) -2-methoxyiminoacetamido]-3-(2-amino-1,2,3,4-thiadiazolyl 5-thiomethyl)-3-cepheme-4-carboxylate.

thiazolyl)-2-methoxyiminoacetamindo]-3-(-2-amino-1,3,4-thiadiazoyl-5-thiomethyl)-3-cepheme -4-carboxyulic acid in living body of the host, the following model experiment was carried out.

As a metabolism-activating enzyme, a rat liver homogenate (S-9, manufactured by Oriental Yeast Co.) was used in the following composition(referred to as S-9 mix, hereinafter):
0.5 ml of S-9
3.3 micromol of potassium chloride
8 micormol of magnesium chloride hexahydrate
5 micromol of glucose-6-phosphate
4 micromol of NADH
4 micromol of NADPH and
0.5 ml of 0.2M phosphoric acid buffer solution of pH of 7.4

After mixing 0.1 ml of a solution of the compound to be tested with 0.9 ml of S-9 mix or 0.9 ml of 0.1 M phosphoric acid buffer solution, the mixture was subjected to shaking culture for 20 min at 37° C. to prepare a test reaction solution for use in the following experiment.

Staphylococcus aureus IAM 1011 was inoculated to Mueller-Hinton'culture medium and the inoculum was cultured for 18 hours at 37° C. and after adjusting the number of the bacterial cells to $10^8$/ml of the culture medium, 50 times by weight of the Mueller-Hinton agar culture medium were added to the cultured medium to prepare flat culture plates. After placing a penicillin-cup of 8 mm in diameter on each of the thus prepared flat culture plates, 0.1 ml of the above-mentioned test reaction solution was introduced into the penicillin cup, and after leaving the system for 2 hours at 4° C., the system was incubated for 18 hours at 37° C., and the diameter of the growth-inhibition circle around the cup on the culture plate was determined.

By applying each of the thus determined diameters of the respective growth-inhibition circles on a diagram preliminarily prepared to indicate the relationship between the diameter of the growth-inhibition circle and the concentration of the compound in the culture medium before carrying out the culture, the concentration of the compound in the culture medium in the presence of S-9 mix was obtained(referred to as $C_2$).

When the concentration of the compound in the cul-

TABLE 2

| Before or after the administration of the compound repr. Formula (V) | $log_{10}$ value of the number of bacterial cells/g of feces | | | | | |
|---|---|---|---|---|---|---|
| | E. coli | Pse. aeruginosa | Streptococcus sp. | Lactobacillus sp. | Lact. bifidus | Bacterioides sp. |
| Before | 6.4 | <3.0 | 6.8 | 9.0 | 8.4 | 8.3 |
| After | 6.5 | <3.0 | 7.0 | 8.9 | 8.4 | 8.2 |

EXAMPLE 6

(1) Stability of the compound represented by the formula (I) and its sodium salt in living body For verifying the stability of the compound represented by the formula (I), 7-beta-[2-(2-amino-4- ture medium in the absence of S-9 mix is referred to $C_1$, the rate of maintaining the anti-bacterial activity is calculated by the following formula:

Rate of maintaining the antibacterial activity (%) = $\frac{C_2}{C_1} \times 100$ The thus calculated values are shown in Table 3.

TABLE 3

| Compound | Rate of maintaining the antibacterial activity (%) |
|---|---|
| Obtained in Ex. 1 | 80 |
| Obtained in Ex. 2 | 78 |
| CEFOTAX ® | 17 |

The results shown in Table 3 indicate that the compound represented by the formula(I) and its sodium salt is stable to the action of rat liver homogenate, namely the metabolism-activating enzyme, and suggest the stability of the compound represented by the formula(I) and its sodium salt in living body.

(2) Stability of the compound represented by the formula(V)

The same test as above was carried on the compound represented by the formula(V). The results obtained were compared to the results of the test (1) on the compound represented by the formula(I) according to the following criterion.

Taking the diameter of the growth-inhibiting circle due to the compound represented by the formula(I) at the same concentration as 100, and the ratio of the diameter of the growth-inhibiting circle due to the compound represented by the fomula(V) to the diameter of the growth-inhibiting circle due to the compound represented by the formula(I) is represented by the percentages as follows, and the respective signs are attributed to the respective percentage.

| Sign | Percentage (range) |
|---|---|
| − | 0 |
| ± | 0 to 1 |
| + | 1 to 33 |
| + + | 33 to 66 |
| + + + | 67 to 100 |

The results of the experiment were shown in Table 4.

TABLE 4

| | added with S-9 mix | without addition of S-9 mix |
|---|---|---|
| Compound represented by Formula (V) | + + + | ± |

The results show that the compound represented by the formula(V) is itself inactive to *Escherichia coli* and after metabolized by the rat liver homogenate, namely, the metabolismactivating enzyme, it becomes active against *Escherichia coli*. The fact suggests that the compound represented by the formula(V) exhibits its antibacterial activity after being absorbed in living body.

EXAMPLE 7

Effect on the experimental infectious disease on mice

To each of the two groups of ddY-strain SPF mice, $1.4 \times 10^8$ cells of *Escherichia coli* was intraperitoneously inoculated to be infected, and just after or after 4 hours of the inoculation, the compound represented by the formula (I) was orally administered at a dose rate of 100 mg/kg. By observing the death of the mice due to the infection for 7 days, it was found that all the control mice (20 mice) inoculated and not administered died on the second day of infection, but more than 55 % of the mice (20 mice) of the groups administered with the compound represented by the formula(I) survived even on the 7th day of infection.

EXAMPLE 8

Stability of the sodium salt of the compound represented by the formula(I) in blood of livinq body A solution of sodium salt (the product in Example 2) of the compound represented by the formula(I) in an aqueous physiological solution was injected into each of 5 healthy male Wistar rats (body weight of about 180 g) after 6 to 7 weeks of birth from the caudal vein by one shot method. The same procedure was carried out by using a solution of the sodium salt in a 1/15 M phosphoric acid buffer of pH of 7.0. After 30 min, 2 hours and 4 hours of the injection, the blood of the rate was collected from the cut carotid artery of the rat, and the collected blood was subjected to centrifugation for 15 min at 3000 rpm to obtain the three kinds of serum specimens (collected after 30 min, 2 hours and 4 hours after the injection).

Separately, flat culture plates were made by adding 0.05 % by weight of *Escherichia coli* IFO 12734 into Heart-infusion agar culture medium, and a penicillin cup of 8 mm in diameter was placed on the flat culture medium, and each of the serum specimen, each of the blood specimen, 1/15 M phosphoric acid buffer solution or a 50% acetone-phosphoric acid buffer solution was introduced into the cup. The thus prepared inoculant was left for 30 min to 1 hour at room temperature and incubated for a night at 37° C.

Then, the diameter of the growth-inhibition circle around the penicillin cup on each flat culture plate was determined, and according to the preliminarily prepared graph showing the relationship between the diameter of the growth-inhibition circle and the concentration of the sodium salt in the serum specimen, the blood specimen, 1/15 M phosphoric acid buffer solution and 50% acetone-phosphoric acid buffer solution, the concentration of the sodium salt in the serum specimen was obtained as:

9.0 micrograms/ml after 30 min of injection,
7.5 micrograms/ml after 2 hours of injection and
2 to 5 micrograms/ml after 4 hours of injection.

On the other hand, by the same experiment except for injecting the same concentration of CEFOTAX ® (manufactured by Hoechst Co., a cephalosporin-derivative) instead of the sodium salt, the following concentration of CEFOTAX ® were found:

7.0 micrograms/ml after 30 min of injection,
2.5 micrograms/ml after 2 hours of injection and
0.4 micrograms/ml after 4 hours of injection.

As will be seen in above, the stability of the sodium salt of the compound represented by the formula(V) according to the present invention is larger than CEFOTAX ®, one of the conventional antibiotic derived from cephalosporin.

EXAMPLE 9

Preparation of the pharmaceutical compositions comprising the compound represented by the formula(I), the sodium salt thereof or the compound represented by the formula(V)

(1) Pellets of the following components:
175 mg of the compound represented by the formula(I) obtained in Example 1,
16 mg of lactose,
3 mg of hydroxypropylcellulose and
1 mg of magnesium stearate.

The compound represented by the formula(I) and lactose were mixed, and after adding an aqueous solution of hydroxypropylcellulose into the mixture, the whole mixture was kneaded, dried and pulverized. After adding magnesium stearate dispersed preliminarily in starch to the pulverized mixture, it was pelletized by a usual method to be pellets each weighing 200 mg.

(2) Granular composition of the following components:
176 mg of the sodium salt of the compound represented by the formula(I), obtained in Example 2,
16 mg of lactose,
4 mg of starch and
4 mg of hydroxypropylcellulose.

The sodium salt, starch and lactose were mixed, and after adding an aqueous solution of hydroxypropylcellulose to the mixture, the whole mixture was kneaded, dried and pulverized. By sifting the thus pulverized mixture and collecting the fraction passing through #12 Taylor standard mesh and stopping on #48 Taylor standard mesh, the granular composition was obtained.

(3) Pellets of the following components:
175 mg of the compound represented by the formula(V) obtained in Example 3,
16 mg of lactose,
3 mg of hydroxypropylcellulose and
1 mg of magnesium stearate.

The compound represented by the formula(V) and lactose were mixed, and after adding an aqueous solution of hydroxypropylcellulose into the mixture, the whole mixture was kneaded, dried and pulverized. After adding magnesium stearate dispersed preliminarily in starch to the pulverized mixture, it was pelletized by a usual method to be pellets each weighing 200 mg.

(4) Granular composition of the following components:
176 mg of the sodium salt of the compound represented by the formula(V), obtained in Example 3,
16 mg of lactose,
4 mg of starch and
4 mg of hydroxypropylcellulose.

The compound represented by the formula(V), starch and lactose were mixed, and after adding an aqueous solution of hydroxypropylcellulose to the mixture, the whole mixture was kneaded, dried and pulverized. By sifting the thus pulverized mixture and collecting the fraction passing through #12 Taylor standard mesh and stopping on #48 Taylor standard mesh, the granular composition was obtained.

What is claimed is:

1. Pivaloyloxymethyl 7-beta-[2-amino-4-thiazolyl)-2-methoxyiminoacetamido]-3-(2-amino-1,3,4-thiadiazolyl -5-thiomethyl)-3-cepheme-4-carboyxlate represented by the following formula:

2. An antibiotic agent comprising as an active ingredient an effective amount of the compound pivaloyloxymethyl 7-beta-[2-(2-amino-4-thiazolyl)-2-methoxyiminoacetamindo]-3-(2-amino-1,3,4-thiadiazolyl-5-thiomethyl) -3-cepheme-4-carboxylate of claim 1.

3. A pharmaceutical composition in dosage unit which comprises an effective dosage of the compound pivaloyloxymethyl 7-beta-[2-(2-amino-4-thiazolyl)-2-methyoxyiminoacetamindo]-3-(2-amino-1,3,4-thiadiazolyl-5-thiomethyl) -3-cepheme-4-carboxylate of claim 1.

4. A method for the treatment of infectious diseases caused by bacteria which comprises administering an effective amount of the compound pivaloyloxymethyl 7-beta-[2-(2-amino-4-thiazolyl)-2-methoxyiminoacetamido]-3-(2-amino-1,3,4-thiadiazolyl-5-thiomethyl) -3-cepheme-4-carboxylate of claim 1.

* * * * *

UNITED STATES PATENT AND TRADEMARK OFFICE
CERTIFICATE OF CORRECTION

PATENT NO. : 4,681,877
DATED : July 21, 1987
INVENTOR(S) : SHIGEAKI MUTO ET AL

It is certified that error appears in the above-identified patent and that said Letters Patent is hereby corrected as shown below:

Amend "ofthe", col. 2, line 46, to read as --of the--.

Incorporate parenthesis --)-- after "thiadiazolyl" in col. 3, line 35.

Amend "thiadiazolyl5", col. 4, line 48, to read as --thiadiazolyl-5".

Amend "cephem", col. 5, line 14, to read as --cepheme--.

Amend "formylamine", col. 6, line 32, to read as --formylamino- --.

UNITED STATES PATENT AND TRADEMARK OFFICE
CERTIFICATE OF CORRECTION

PATENT NO. : 4,681,877
DATED : July 21, 1987
INVENTOR(S) : SHIGEAKI MUTO ET AL

Page 2 of 2

It is certified that error appears in the above-identified patent and that said Letters Patent is hereby corrected as shown below:

Amend "1,3,4thiadiazolyl" col. 15, lines 15-16, to read as --1,3,4-thiadiazolyl--.

Amend "thiadiazolyl 5", col. 15, line 54, to read as --thiadiazolyl-5--.

Signed and Sealed this

Twenty-sixth Day of April, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,681,877
DATED      : July 21, 1987
INVENTOR(S) : SHIGEAKI MUTO ET AL It is certified that error appears in the above-identified patent and that said Letters Patent is hereby corrected as shown below:

Amend "2-AMINO-1,3-" in the title of invention on first page and col. 1, to read as --2-AMINO-1,3,4-...--.

Amend "thiomethyl-3-cepheme-3-carboxylic" bridging from col. 11, last line, to col. 12, line 1, to read as --thiomethyl)-3-cepheme-4-carboxylic...--.

Signed and Sealed this

Nineteenth Day of July, 1988

Attest:

DONALD J. QUIGG

Attesting Officer

Commissioner of Patents and Trademarks